United States Patent [19]

Reiffen et al.

[11] Patent Number: 4,616,011
[45] Date of Patent: Oct. 7, 1986

[54] NOVEL INDOLE DERIVATIVES AND PHARMACEUTICAL COMPOSITIONS CONTAINING SAME

[75] Inventors: Manfred Reiffen, Biberach; Joachim Heider, Warthausen; Volkhard Austel; Norbert Haüel, both of Biberach, all of Fed. Rep. of Germany; Walter Kobinger; Christian Lillie, both of Vienna, Austria

[73] Assignee: Dr. Karl Thomae GmbH, Biberach an der Riss, Fed. Rep. of Germany

[21] Appl. No.: 675,084

[22] Filed: Nov. 26, 1984

[30] Foreign Application Priority Data

Dec. 3, 1983 [DE] Fed. Rep. of Germany ....... 3343801

[51] Int. Cl.⁴ .................... A61K 31/55; C07D 403/12; C07D 405/14
[52] U.S. Cl. .................................. 514/221; 540/500; 540/523; 540/534; 514/213; 514/215; 514/220; 540/495; 540/521; 540/587
[58] Field of Search .................. 260/239.3 B, 239.3 T, 260/245.7; 514/213, 215, 220, 221

[56] References Cited

U.S. PATENT DOCUMENTS 4,137,318 1/1979 Eberlein et al. .............. 260/239.3 B
4,490,369 12/1984 Reiffen et al. ................ 260/239.3 B Primary Examiner—Robert T. Bond
Attorney, Agent, or Firm—Hammond & Littell, Weissenberger & Dippert

[57] ABSTRACT

This invention relates to novel indole derivatives of the formula

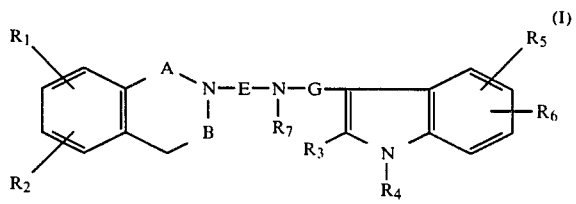

wherein
A represents a $-CH_2-CH_2-$, $-CH=CH-$,

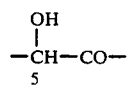

group and B represents a methylene, carbonyl, or thiocarbonyl group or
A represents a $-CO-CO-$ or $$-\underset{5}{\underset{|}{\overset{OH}{\underset{CH}{|}}}}-CO-$$

group and B represents a methylene group,
E represents an alkylene group or a 2-hydroxy-n-propylene, 2-hydroxy-n-butylene, or 3-hydroxy-n-butylene group,
G represents an alkylene group,
$R_1$ represents a hydrogen, chlorine, or bromine atom or a trifluoromethyl, nitro, amino, alkylamino, dialkylamino, alkyl, hydroxyl, alkoxy, or phenylalkoxy group,
$R_2$ represents a hydrogen, chlorine, or bromine atom or a hydroxyl, alkoxy, phenylalkoxy, or alkyl group or
$R_1$ and $R_2$ together represent an alkylenedioxy group,
$R_3$ represents a hydrogen, chlorine, or bromine atom or an alkyl group,
$R_4$ represents a hydrogen atom or an alkyl or phenylalkyl group,
$R_5$ represents a hydrogen, fluorine, chlorine, or bromine atom or an alkyl, hydroxyl, alkoxy, or phenylalkoxy group,
$R_6$ represents a hydrogen atom or an alkoxy group, and
$R_7$ represents a hydrogen atom or an alkenyl, alkyl or phenylalkyl group,
and the acid additional salts thereof. These compounds, which may be obtained by use of known methods, have valuable pharmacological properties, particularly a heart rate-lowering activity.

8 Claims, No Drawings

NOVEL INDOLE DERIVATIVES AND PHARMACEUTICAL COMPOSITIONS CONTAINING SAME

The present invention relates to novel indole derivatives of the formula

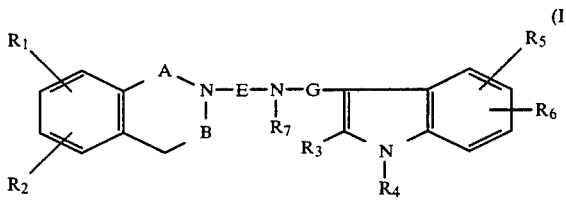

and the acid addition salts thereof, particularly the pharmacologically acceptable acid addition salts with inorganic or organic acids. The invention also relates to processes for preparing these compounds and to pharmaceutical compositions containing them.

The novel compounds have valuable pharmacological properties. They especially have a long-lasting heart rate-reducing activity and the effect of reducing the oxygen requirements of the heart.

In Formula I,

A represents a $-CH_2-CH_2-$, $-CH=CH-$,

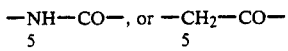

group and B represents a methylene, carbonyl, or thiocarbonyl group or,

A represents a $-CO-CO-$ or

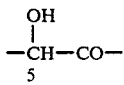

group and B represents a methylene group,

E represents a linear alkylene group having from 2 to 4 carbon atoms, optionally substituted by an alkyl group having from 1 to 3 carbon atoms, or a 2-hydroxy-n-propylene, 2-hydroxy-n-butylene, or 3-hydroxy-n-butylene group, G represents a linear alkylene group having from 1 to 5 carbon atoms, optionally substituted by an alkyl group having from 1 to 3 carbon atoms, $R_1$ represents a hydrogen, chlorine, or bromine atom or a trifluoromethyl, nitro, amino, alkylamino, dialkylamino, alkyl, hydroxyl, alkoxy, or phenylalkoxy group, where each alkyl moiety may have from 1 to 3 carbon atoms, $R_2$ represents a hydrogen, chlorine, or bromine atom, or a hydroxyl, alkoxy, phenylalkoxy, or alkyl group, where each alkyl moiety may have from 1 to 3 carbon atoms, or $R_1$ and $R_2$ together represent an alkylenedioxy group having 1 or 2 carbon atoms, $R_3$ represents a hydrogen, chlorine, or bromine atom or an alkyl group having from 1 to 4 carbon atoms, $R_4$ represents a hydrogen atom or an alkyl or phenylalkyl group, where each alkyl moiety may have from 1 to 3 carbon atoms, $R_5$ represents a hydrogen, fluorine, chlorine, or bromine atom or an alkyl, hydroxyl, alkoxy, or phenylalkoxy group, where each alkyl moiety may have from 1 to 3 carbon atoms, $R_6$ represents a hydrogen atom or an alkoxy group having from 1 to 3 carbon atoms, and $R_7$ represents a hydrogen atom, an alkenyl group having from 3 to 5 carbon atoms, or an alkyl or phenylalkyl group, where the alkyl moiety may contain from 1 to 3 carbon atoms.

Examples of the above-defined groups include the following:

$R_1$ may represent a hydrogen, chlorine, or bromine atom or a methyl, ethyl, n-propyl, isopropyl, trifluoromethyl, hydroxyl, methoxy, ethoxy, n-propoxy, isopropoxy, nitro, amino, methylamino, ethylamino, n-propylamino, isopropylamino, dimethylamino, diethylamino, di-n-propylamino, diisopropylamino, methyl-ethylamino, methyl-n-propylamino, methyl-isopropylamino, ethyl-n-propylamino, benzyloxy, 1-phenylethoxy, 1-phenylpropoxy, 2-phenylethoxy, or 3-phenylpropoxy group, $R_2$ may represent a hydrogen, chlorine, or bromine atom or a methyl, ethyl, n-propyl, isopropyl, hydroxyl, methoxy, ethoxy, n-propoxy, isopropoxy, benzyloxy, 1-phenylethoxy, 2-phenylethoxy, 2-phenylpropoxy, or 3-phenylpropoxy group, or together with $R_1$ represents the methylenedioxy or ethylenedioxy group, $R_3$ may represent a hydrogen, chlorine, or bromine atom or a methyl, ethyl, n-propyl, isopropyl, n-butyl, isobutyl, or tert.butyl group, $R_4$ may represent a hydrogen atom or a methyl, ethyl, n-propyl, isopropyl, benzyl, 1-phenylethyl, 2-phenylethyl, or 3-phenylpropyl group, $R_5$ may represent a hydrogen, fluorine, chlorine, or bromine atom or a methyl, ethyl, n-propyl, isopropyl, hydroxyl, methoxy, ethoxy, n-propoxy, isopropoxy, benzyloxy, 1-phenylethoxy, 2-phenylethoxy, 1-phenylpropoxy, or 3-phenylpropoxy group, $R_6$ may represent a hydrogen atom or a methoxy, ethoxy, n-propoxy, or isopropoxy group, $R_7$ may represent a hydrogen atom or a methyl, ethyl, n-propyl, isopropyl, benzyl, 1-phenylethyl, 2-phenylethyl, 1-phenylpropyl, 1-methyl-1-phenylethyl, 3-phenylpropyl, allyl, n-buten-(2)-yl, or n-penten-(2)-yl group, E may represent an ethylene, n-propylene, n-butylene, 1-methylethylene, 2-ethyl-ethylene, 1-propyl-ethylene, 1-methyl-n-propylene, 2-methyl-n-propylene, 1-ethyl-n-propylene, 3-ethyl-n-propylene, 2-propyl-n-propylene, 2-methyl-n-butylene, 2-hydroxy-n-propylene, 2-hydroxy-n-butylene, or 3-hydroxy-n-butylene group, and G may represent a methylene, ethylidene, n-propylidene, n-butylidene, 2-methyl-propylidene, ethylene, 1-methylethylene, 2-ethyl-ethylene, 1-propyl-ethylene, 2-methylethylene, n-propylene, n-butylene, n-pentylene, 1-methyl-n-propylene, 1-methyl-n-butylene, 1-methyl-n-pentylene, 1-ethyl-n-propylene, 2-ethyl-n-propylene, or 1-ethyl-n-butylene group, preferably while $R_1$ is in the 7-position and $R_2$ is in the 8-position of the phenyl nucleus.

The preferred compounds are the compounds of the formula

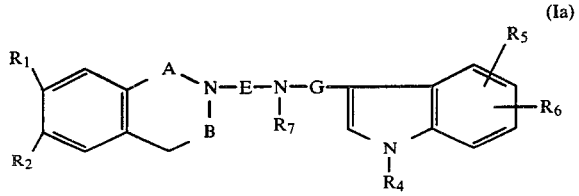

wherein
A and B are as hereinbefore defined,
E represents an n-propylene group,
G represents an ethylene or n-propylene group,
R represents a chlorine or bromine atom, or a methyl, methoxy, nitro, amino, methylamino, or dimethylamino group,
Rhd 2 represents a hydrogen, chlorine, or bromine atom or a methoxy group, or $R_1$ and $R_2$ together represent a methylenedioxy group,
$R_4$ represents a hydrogen atom or a methyl group,
$R_5$ represents a hydrogen, fluorine, chlorine, or bromine atom or a methyl, hydroxyl, methoxy, or benzyloxy group,
$R_6$ represents a hydrogen atom or a methoxy group, and
$R_7$ represents a hydrogen atom or a methyl group,
and the acid addition salts thereof, particularly the pharmacologically acceptable acid addition salts with inorganic or organic acids.

However, the particularly preferred compounds of Formula Ia above are those wherein
A represents a —CH$_2$CH$_2$— or —CH=CH— group and B represents a carbonyl group or
A represents a —COCO— or —NHCO— group and B represents a methylene group,
E represents an n-propylene group,
G represents an ethylene group,
$R_1$ and $R_2$ each represent a methoxy group,
$R_4$, $R_5$, and $R_6$ each represent a hydrogen atom, and
$R_7$ represents a methyl group,
and the acid addition salts thereof, particularly the pharmacologically acceptable acid addition salts with inorganic or organic acids.

According to the invention the compounds of Formula Ia are obtained by the following processes:

Method A

A compound of the formula

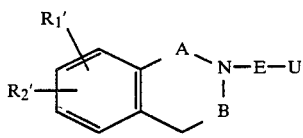

is reacted with a compound of the formula

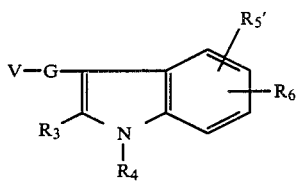

wherein
$R_3$, $R_4$, $R_6$, A, B, E, and G are as hereinbefore defined, $R_1'$ represents a hydroxyl, amino, or alkylamino group protected by a protecting group or has the meanings given for $R_1$ hereinbefore,
$R_2'$ represents a hydroxyl group protected by a protecting group or has the meanings given for $R_2$ hereinbefore,
$R_5'$ represents a hydroxyl group protected by a protecting group or has the meanings given for $R_5$ hereinbefore, and
one of U and V represents the group $R_7'$—NH—, wherein $R_7'$ represents a protecting group for an amino group or has the meanings given for $R_7$ hereinbefore, and the other of U and V represents a nucleophilic leaving group such as a halogen atom or a sulfonyloxy group, e.g., a chlorine, bromine, or iodine atom or a methanesulfonyloxy, p-toluenesulfonyloxy, or ethoxylsulfonyloxy group.

Optionally any protecting group used is subsequently split off.

Examples of protecting groups for a hydroxyl group include the trimethylsilyl, acetyl, benzoyl, benzyl, and tetrahydropyranyl groups, and examples of protecting groups for an amino or alkylamino group include the acetyl, benzoyl, ethoxycarbonyl, and benzyl groups.

The reaction is conveniently carried out in a solvent or mixture of solvents such as acetone, diethyl ether, methylformamide, dimethylformamide, dimethylsulfoxide, benzene, chlorobenzene, tetrahydrofuran, benzene/tetrahydrofuran, or dioxane or in an excess of the compounds of Formulae II and/or III used and optionally in the presence of an acid-binding agent, e.g., an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, the latter of which may also be used simultaneously as solvent, or a reaction accelerator such as potassium iodide, advantageously at temperatures of from about 0° to 150° C., dependent upon the reactivity of the nucleophilically exchangeable group, preferably at temperatures of from about 50° to 120° C., e.g., at the boiling temperature of the solvent used. However, the reaction may also be carried out without a solvent. It is particularly advantageous to carry out the reaction in the presence of a tertiary organic base or an excess of the amine of Formula III used.

The optional subsequent splitting off of any protecting group used is preferably carried out hydrolytically in an aqueous solvent, e.g., in water, isopropanol/water, tetrahydrofuran/water, or dioxane/water, in the presence of an acid such as hydrochloric or sulfuric acid or in the presence of an alkali metal base such as sodium hydroxide or potassium hydroxide at temperatures of from about 0° to 100° C., preferably at the boiling temperature of the reaction mixture. However, the splitting off of a benzyl group is preferably carried out by hydrogenolysis, e.g., with hydrogen in the presence of a catalyst such as palladium/charcoal, in a solvent such as methanol, ethanol, ethyl acetate, or glacial acetic acid, optionally with the addition of an acid such as hydrochloric acid, at temperatures of from about 0° to 50° C., preferably at ambient temperature, and under a hydrogen pressure of from about 1 to 7 bar, preferably from about 3 to 5 bar.

Method B

To prepare compounds of Formula I wherein B represents a thiocarbonyl group, a compound of the formula

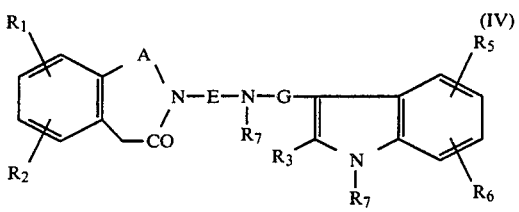

wherein $R_1$ to $R_7$, A, E, and G are as hereinbefore defined, is reacted with an agent which introduces sulfur. The reaction is carried out in a sulfur-introducing agent such as phosphorus pentasulfide or 2,4-bis(4-methoxyphenyl)-1,3-dithia-2,4-diphosphetan-2,4-disulfide, advantageously in a solvent such as toluene or xylene, at temperatures of from about 50° to 150° C., e.g., at the boiling temperature of the reaction mixture.

Method C

To prepare compounds of Formula I wherein A represents a

group, a compound of the formula

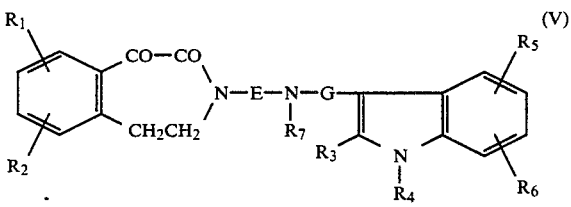

wherein $R_1$ to $R_7$, E, and G are as hereinbefore defined, is reduced. The reaction is carried out in the presence of a suitable reducing agent such as a metal hydride, e.g., sodium borohydride, in a suitable solvent such as water/methanol or methanol/ether, at temperatures of from about 0° to 80° C., preferably at temperatures of from about 15° to 40° C.

Method D

To prepare compounds of Formula I wherein A represents a —CH$_2$—CH$_1$— or —CH=CH— group and B represents a methylene group, a compound of the formula

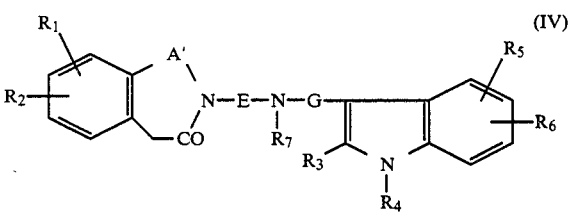

wherein $R_1$ to $R_7$, E, and G are as hereinbefore defined and A' represents a —CH$_2$—CH$_2$— or —CH=CH— group, is reduced. The reduction is preferably carried out with a metal hydride such as lithium aluminium hydride or diborane or with a complex of borane and a thioether, e.g., with borane-dimethylsulfide complex, in a suitable solvent such as diethyl ether or tetrahydrofuran at temperatures of from about 0° to 50° C., preferably at temperatures of from about 10° to 25° C.

Method E

To prepare compounds of Formula I wherein A represents the —COCO— group, a compound of the formula

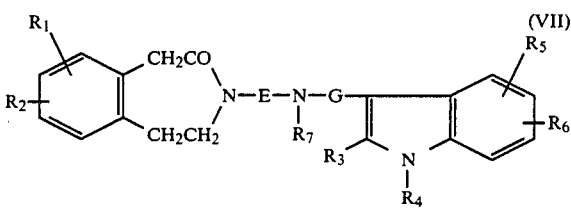

wherein $R_1$ to $R_7$, E, and G are as hereinbefore defined, is oxidized. The oxidation is preferably carried out with an oxidizing agent such as potassium permanganate, selenium dioxide, or sodium dichromate in a suitable solvent or mixture of solvents such as water/dioxane, glacial acetic acid, water/acetic acid, or acetic anhydride, at temperatures of from about 0° to 100° C., preferably at temperatures of from about 20° to 80° C.

Method F

To prepare compounds of Formula I wherein A represents a —NH—CO— group and E represents an alkylene group having from 2 to 4 carbon atoms, optionally substituted by an alkyl group having from 1 to 3 carbon atoms, a compound of the formula

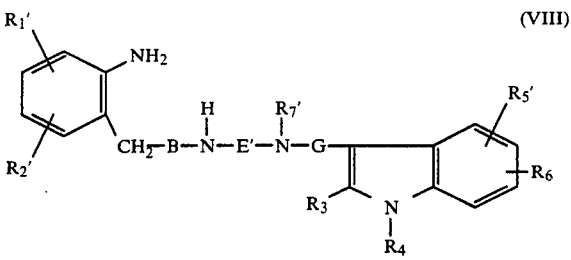

wherein

B, G, $R_3$, $R_4$, and $R_6$ are as hereinbefore defined,

E' represents an alkenyl group having from 2 to 4 carbon atoms, optionally substituted by an alkyl group having from 1 to 3 carbon atoms, $R_1'$ represents a hydroxyl, amino, or alkylamino group protected by a protecting group, or has the meanings given for $R_1$ hereinbefore, $R_2'$ represents a hydroxyl group protected by a protecting group or has the meanings given for $R_2$ hereinbefore, $R_5'$ represents a hydroxyl group protected by a protecting group or has the meanings given for $R_5$ hereinbefore, $R_7'$ represents a protecting group for an amino group or has the meanings given for $R_7$ hereinbefore, with the exception of hydrogen, is reacted with a carbonic acid derivative of the formula $$W-CO-W \quad (IX)$$

wherein each W, which may be identical or different, represents a nucleophilic leaving group such as a chlorine or bromine atom, an alkoxy group having from 1 to 3 carbon atoms, or an imidazolyl-(1) group. Optionally any protecting group used is subsequently split off.

Suitable protecting groups for a hydroxyl group include the trimethylsilyl, acetyl, benzoyl, benzyl, and tetrahydropyranyl groups, and examples of protecting groups for an amino or alkylamino group include the acetyl, benzoyl, ethoxycarbonyl and benzyl groups.

The reaction is appropriately carried out in a solvent or mixture of solvents such as methylene chloride, carbon tetrachloride, benzene, tetrahydrofuran, benzene/tetrahydrofuran, dioxane, or acetonitrile, advantageously at temperatures of from about 0° to 150° C., preferably at the boiling temperature of the solvent used, e.g., at temperatures of from about 40° to 100° C., and optionally in the presence of an acid-binding agent such as potassium carbonate, sodium hydroxide, potassium hydroxide, pyridine, or triethylamine, the latter possibly also acting as solvent. However, the reaction may also be carried out without a solvent. If in a compound of Formula IX used at least one of the groups W represents an alkoxy group having from 1 to 3 carbon atoms, the reaction is preferably carried out in an excess of the ester used as solvent.

The optional subsequent splitting off of any protecting group used is preferably carried out hydrolytically in an aqueous solvent, e.g., in water, isopropanol/water, tetrahydrofuran/water, or dioxane/water, in the presence of an acid such as hydrochloric or sulfuric acid or in the presence of an alkali metal base such as sodium hydroxide or potassium hydroxide at temperatures of from about 0° to 100° C., preferably at the boiling temperature of the reaction mixture. However, the splitting off of a benzyl group may also be effected by hydrogenolysis, e.g., with hydrogen in the presence of a catalyst such as palladium/charcoal, in a solvent such as methanol, ethanol, ethyl acetate, or glacial acetic acid, optionally with the addition of an acid such as hydrochloric acid, at temperatures of from about 0° to 50° C., preferably at ambient temperature, and under a hydrogen pressure of from about 1 to 7 bar, preferably from about 3 to 5 bar.

The compounds of Formula I obtained may also be converted into their acid addition salts, particularly the pharmacologically acceptable acid addition salts thereof with inorganic or organic acids. Suitable acids include, for example, hydrochloric, hydrobromic, sulfuric, phosphoric, acetic, lactic, citric, tartaric, succinic, maleic, and fumaric acid.

The compounds of Formulae II to IX used as starting materials are known from the literature in some cases or may be obtained by methods known per se.

Thus, for example, a starting compound of Formula II is obtained by reacting a corresponding benzazepine with a corresponding halogen compound and optionally subsequently reacting with a corresponding amine. The corresponding benzazepine unsubstituted in the 3-position required for this is obtained by cyclizing a corresponding compound, e.g., by cyclizing a compound of the formula

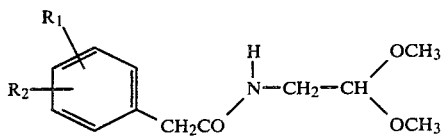
(X)

or

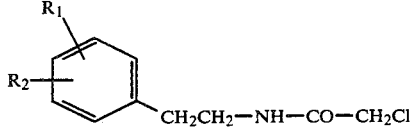
(XI)

and optionally subsequently carrying out catalytic hydrogenation and/or reduction of the carbonyl group, for example, with sodium borohydride/glacial acetic acid (see EP-A No. 0,007,070, incorporated herein by reference) and/or oxidation, e.g., with selenium dioxide.

A compound of Formulae IV to VII used as starting material is preferably obtained by reacting a corresponding halogen compound with a corresponding amine and optoinally subsequently splitting off any protecting groups used to protect the hydroxyl and/or amino groups. A compound of Formula VIII used as starting material is obtained, for example, by reduction of a corresponding nitro compound.

As mentioned above, the compounds of Formula I and the pharmacologically acceptable acid addition salts thereof with inorganic or organic acids have valuable pharmacological properties, particularly with few side effects, e.g., a slight antimuscarinic activity, a long-lasting heart rate-reducing activity and a reduction in the oxygen requirement of the heart. They also have an α-blocking effect. To demonstrate these properties, the compounds A = 1-(7,8-Dimethoxy-1,3,4,5-tetrahydro-2H-3-benzazepin-2-on-3-yl)-3-[N-methyl-N-(2-(indolyl-3)-ethyl)-amino]-propane, and B = 1-(7,8-Dimethoxy-1,3,4,5-tetrahydro-2H-3-benzazepin-1,2-dion-3-yl)-3-[N-methyl-N-(2-(indolyl-3)-ethyl)-amino]-propane for example, were tested for their biological properties as follows:

Effect on Heart Rate in Rats

The activity of the substances to be tested on heart rate was investigated on two rats with an average weight of from 250 to 300 gm for each dosage. The rats were anaesthetised with pentobarbital (50 mg/kg i.p. and 20 mg/kg s.c.). The test substances were injected in aqueous solution into the jugular vein (0.1 ml/100 gm).

The blood pressure was measured by means of a cannula inserted in a carotid artery, and the heart rate was recorded from an ECG (2nd or 3rd branch) taken with needle electrodes. The heart rate of the animals in the control period was between 350 and 400 beats per minute (b/min).

The results obtained are set forth in the following table:

TABLE

| Substance | Dosage (mg/kg) | Reduction in Heart Rate, Measured 20 Minutes After Administration of Substance (b/min) |
|---|---|---|
| A | 5.0 | −153 |
|   | 2.5 | −143 |
|   | 1.0 | −99 |
| B | 5.0 | −128 |

The compounds prepared according to the invention have no toxic side effects at all when used in therapeutic doses. Thus, for example, when substance A is administered intravenously, even in a high dose of 20 mg/kg in mice, no toxic side effects were observed.

In view of their pharmacological properties, the compounds prepared according to the invention are suitable for the treatment of sinus tachycardia of various origins and for the prophylaxis and therapy of ischaemic heart diseases. For these purposes, the compounds of Formula I and the pharmacologically acceptable acid addition salts thereof, optionally in combination with other active ingredients, preferably substances which additionally guard against infection by microbes, such as sulfonamides or antibiotics, e.g., tetracycline, doxycycline, ampicillin, amoxycillin, cephalexin, or erythromycin, may be administered to warm-blooded hosts perorally, parenterally, or rectally as active ingredients in customary preparation forms suitable for the intended purposes, that is, compositions consisting essentially of one or more inert conventional carriers and/or diluents, e.g., corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, carboxymethylcellulose, or fatty substances such as hard fat, or suitable mixtures thereof, and an effective amount of the active ingredient, such as tablets, coated tablets, capsules, powders, suppositories, syrups, solutions, suspensions, emulsions, ampules, and drops. Advantageously the active ingredient or a mixture of different active ingredients of Formula I may be administered orally to both humans or animals, in a single dose of from about 2.25 to 30 mg (0.03 to 0.4 mg/kg of body weight), preferably from about 5.25 to 18.75 mg (0.07 to 0.25 mg/kg of body weight), once or twice a day. A daily dose is therefore from about 2.25 to 60 mg (from about 0.03 to 0.8 mg/kg of body weight), preferably from about 5.25 to 37.5 mg (from about 0.07 to 0.5 mg/kg of body weight). Dependent upon the type and body weight of the patient to be treated, upon the type and severity of the affliction, upon the type of preparation and upon the route of administration as well as on the period or interval over which the administration takes place it may, however, be necessary to deviate from the above dosages. Thus, it may be sufficient in some cases to administer more or less than the above-mentioned amounts of active ingredient. The optimum dosage and route of administration of the active ingredients which are necessary in each case can easily be determined by one skilled in the art.

The following examples are intended to illustrate the invention and should not be construed as limiting the invention thereto.

EXAMPLES

Preparation of the Starting Compounds

EXAMPLE A 7,8-Dimethoxy-1,3-dihydro-2H-3-benzazepin-2-one (a) 3,4-Dimethoxy-phenylacetyl chloride Over a period of two hours, 600 ml of thionyl chloride are added dropwise, under stirring, to a suspension of 549.4 gm of 3,4-dimethoxy-phenylacetic acid in 600 ml of methylene chloride. After the development of gas has ended (16 hours), the mixture is refluxed for a further hour. Once the highly volatile components have been removed, the residue is distilled in vacuo.

Yield: 486 gm (80.8% of theory),
B.P.: 134°–136° C./1.95 mbar.

(b) N-(2,2-Dimethoxyethyl)-3,4-dimethoxy-phenylacetamide

A solution of 485.2 gm of 3,4-dimethoxyphenylacetyl chloride in 1.1 liters of methylene chloride is added dropwise at 15° to 20° C. to a solution of 246.2 ml of aminoacetaldehyde dimethylacetal and 315 ml of triethylamine in 2.2 liters of methylene chloride, while the mixture is cooled with ice, and then the mixture is stirred for a further hour at 16° to 18° C. It is then extracted several times with water, dried over magnesium sulfate, and concentrated by evaporation. The resulting oil slowly crystallizes out.

Yield: 608 gm (95% of theory),
M.P.: 66°–69° C.

(c) 7,8-Dimethoxy-1,3-dihydro-2H-3-benzazepin-2-one

A solution of 600.6 gm of N-(2,2-dimethoxyethyl)-3,4-dimethoxy-phenylacetamide in 3 liters of concentrated hydrochloric acid is mixed with 3 liters of glacial acetic acid. After standing for 17 hours at ambient temperature, the mixture is poured onto ice. The crystals precipitated are subjected to suction filtration, washed with water until neutral, and dried.

Yield: 350 g (75.4% of theory),
M.P.: 234°–237° C.

EXAMPLE B 7,8-Dimethoxy-1,3,4,5-tetrahydro-2H-3-benzazepin-2-one

A suspension of 21.9 gm (0.1 mol) of 7,8-dimethoxy-1,3-dihydro-2H-3-benzazepin-2-one and 1.5 gm of 10% palladium/charcoal in 200 ml of glacial acetic acid is hydrogenated at 50° C. under a hydrogen pressure of 5 bar. After the catalyst has been filtered off, the solvent is concentrated by evaporation in vacuo, and the residue is taken up in methylene chloride. After extraction with sodium bicarbonate solution and washing with water, the product is dried over magnesium sulfate, evaporated, and purified over silica gel with methylene chloride and then with increasing amounts of methanol (up to 10%).

Yield: 12.6 gm (57% of theory),
M.P.: 188°–191° C.

EXAMPLE C 7,8-Dimethoxy-2,3,4,5-tetrahydro-1H-3-benzazepine

A solution of 1.8 gm of glacial acetic acid in 10 ml of dioxane is added dropwise to a suspension of 1.3 gm (6 mmol) of 7,8-dimethoxy-1,3,4,5-tetrahydro-2H-3-benzazepin-2-one and 1.1 gm (3 mmol) of sodium borohydride in 20 ml of dioxane, and the resulting mixture is refluxed for three hours, concentrated by evaporation, and mixed with water. The mixture is extracted twice with methylene chloride, the extract is concentrated by evaporation, and the residue is taken up in ether. After filtration, the ether is removed in vacuo.

Yield: 1.1 gm (92.7% of theory),
M.P.: 86°–89° C.

EXAMPLE D 6,9-Dimethoxy-1,3-dihydro-2H-3-benzazepin-2-one

Two grams (0.007 mol) of N-(2,2-dimethoxyethyl)-2,5-dimethoxyphenyl-acetamide have 3 ml of polyphosphoric acid poured over, and the mixture is stirred for 60 minutes at 90° C. Then ice water is added, and the product precipitated is subjected to suction filtration and dried.

Yield: 0.98 gm (64% of theory),
M. P. 188°–191° C.

EXAMPLE E 7,8-Dimethyl-1,3-dihydro-2H-3-benzazepin-2-one

Prepared analogously to Example D from N-(2,2-dimethoxyethyl)-3,4-dimethyl-phenylacetamide and polyphosphoric acid.

Yield: 40.1% of theory,
M.P.: 220°–224° C.

EXAMPLE F 7,8-Dimethoxy-1,3,4,5-tetrahydro-2H-3-benzazepin-2,4-dione (a)

7,8-Dimethoxy-2-amino-4-bromo-1H-3-benzazepine-hydrobromide

An amount of 3.7 gm (0.017 mol) of 3,4-dimethoxy-o-phenylenediacetonitrile is suspended in 10 ml of glacial acetic acid and then combined at 20° C. with 12 ml of 30% hydrobromic acid in glacial acetic acid. The mixture is stirred for a further three hours at ambient temperature, and the precipitate is subjected to suction filtration, washed with glacial acetic acid and then with acetone/ether, and dried.

Yield: 5.3 gm (82.8% of theory),
M.P.: 210°–211° C. (decomposition).

(b)

7,8-Dimethoxy-1,3,4,5-tetrahydro-2H-3-benzazepin-2,4-dione

A quantity of 5.3 gm (0.014 mol) of 7,8-dimethoxy-2-amino-4-bromo-1H-3-benzazepine hydrobromide is dissolved in 100 ml of hot water at 85° C., mixed with 1.3 gm of anhydrous sodium acetate, and heated to 90° C. for one hour. The reaction mixture is cooled, subjected to suction filtration, washed with cold water, and dried.

Yield: 2.9 gm (88% of theory),
M.P.: 235° C. (decomp).

EXAMPLE G

N-[3-(7,8-Dimethoxy-1,3,4,5-tetrahydro-2H-3-benzazepin-2-on-3-yl)-propyl]-methylamine hydrochloride Prepared analogously to Example B by catalytic hydrogenation of 1-(7,8-dimethoxy-1,3-dihydro-2H-3-benzazepin-2-on-3-yl)-3-(N-benzyl-methylamino)-propane.

Yield: 87% of theory,
M.P.: 110° C. (decomp).

EXAMPLE H 7,8-Dimethoxy-2,3-dihydro-1H-3-benzazepine

A boiling suspension of 0.8 gm of lithium aluminium hydride in 100 of absolute dioxane is mixed with 2.2 gm (0.01 mol) of 7,8-dimethoxy-1,3-dihydro-2H-3-benzazepin-2-one and then refluxed for three hours. While the mixture is cooled with ice, 10% ammonium chloride solution is added, and the precipitate formed is subjected to suction filtration. The filtrate is concentrated in vacuo to a volume of about 20 ml, and the white precipitate is subjected to suction filtration and washed with a small amount of dioxane, Yield: 0.9 gm (43.8% of theory),
M.P.: 162°–163° C.

EXAMPLE I 1-(7,8-Dimethoxy-1,3,4,5-tetrahydro-2H-3-benzazepin-2-on-3-yl)-3-chloro-propane (a)

1-(7,8-Dimethoxy-1,3-dihydro-2H-3-benzazepin-2-on-3-yl)-3-chloro-propane

An amount of 131.5 gm (0.6 mol) of 7,8-dimethoxy-1,3-dihydro-2H-3-benzazepin-2-one is suspended in 900 ml of dimethylsulfoxide and mixed with 80.8 gm (0.72 mol) of potassium tert.butoxide, with stirring. After ten minutes the solution obtained is added dropwise to 77 ml (0.72 mol) of 1-bromo-3-chloropropane in 300 ml of dimethylsulfoxide, while the mixture is cooled with ice water. After one hour, it is poured onto ice water, and shortly afterwards the greasy precipitate starts to crystallize. The precipitate is subjected to suction filtration, dissolved in acetone, precipitated again with water, subjected to suction filtration, and dried.

Yield: 155.5 gm (87.3% of theory),
M.P.: 101°–103° C.

(b)

1-(7,8-Dimethoxy-1,3,4,5-tetrahydro-2H-3-benzazepin-2-on-3-yl)-3-chloro-propane

A quantity of 59.2 gm (0.2 mol) of 1-(7,8-dimethoxy-1,3-dihydro-2H-3-benzazepin-2-on-3-yl)-3-chloro-propane is hydrogenated in 500 ml of glacial acetic acid in the presence of 5 gm of 10% palladium/charcoal for six hours at 50° C. under a pressure of 5 bar. The catalyst is removed by suction filtration, the glacial acetic acid is distilled off in vacuo, and the residue is neutralized with potassium carbonate, after the addition of water. The precipitate is subjected to suction filtration, washed with water until free from salt, and then dried.

Yield: 53 gm (89% of theory),
M.P. 85°–86° C.

EXAMPLE J 3-(N-Methyl-2-amino-ethyl)-indole (a) 3-(N-formyl-2-amino-ethyl)-indole An amount of 20.5 gm (0.128 mol) of tryptamine in the form of a suspension in 400 ml of toluene is mixed with 5.3 ml (0.14 mol) of formic acid. After 14 hours' boiling with use of a water separator, during which time 5.3 ml (0.14 mol) of formic acid are added every two hours, the mixture is concentrated by rotation, dissolved in methylene chloride, extracted with water, dried over magnesium sulfate, rotated again, and purified over 2000 gm of aluminium oxide (neutral; activity II) with methylene chloride and then with increasing amounts of ethanol (up to 100%).

Yield: 23.8 gm (98.8% of theory),

IR-spectrum (methylene chloride): 1695 cm$^{-1}$ C=O.

(b) 3-(N-Methyl-2-amino-ethyl)-indole

A suspension of 6.8 gm (0.18 mol) of lithium aluminium hydride in 150 ml of absolute tetrahydrofuran is mixed with 23.6 gm (0.125 mol) of 3-(N-formyl-2-amino-ethyl)-indole and then refluxed for 12 hours. While the mixture is cooled with ice water, it is decomposed with water and 15% sodium hydroxide solution, and the precipitate formed is subjected to suction filtration. The filtrate is concentrated by evaporation in vacuo and purified over 2000 gm of aluminium oxide (neutral; activity II) with methylene chloride and increasing amounts of ethanol (up to 20%).

Yield: 19.6 gm (89.9% theory),

IR-spectrum (methylene chloride): 3490 cm$^{-1}$ (indole).

EXAMPLE K

5-Methoxy-3-(N-methyl-2-amino-ethyl)-indole (a) 5-Methoxy-indolyl-3-(N-methyl-glyoxamide)

A solution of 7.9 gm (0.054 mol) of 5-methoxy-indole in 160 ml of absolute ether is mixed with 4.3 ml (0.06 mol) of oxalyl chloride, under cooling with ice. The precipitate obtained is subjected to suction filtration, briefly dried, and added to 100 ml of 40% aqueous methylamine solution, under cooling with ice. After 30 minutes it is subjected to suction filtration, washed with water, and dried.

Yield: 9.55 gm (84.3% of theory),

M.P.: 206°–207° C.

(b) 5-Methoxy-3-(N-methyl-2-amino-ethyl)-indole

A solution of 4.64 gm (0.02 mol) of 5-methoxy-indolyl-3-(N-methyl-glyoxamide) and 12.3 ml (0.1 mol) of boron trifluoridediethyl ether complex in 1000 ml of absolute tetrahydrofuran is mixed, under a current of nitrogen, with 60 ml (0.12 mol) of a 2 molar solution of borane-dimethylsulfide complex. After being stirred for 70 hours at ambient temperature, the mixture is concentrated by evaporation in vacuo and purified over 900 gm of aluminium oxide (neutral; activity II) with methylene chloride and then with increasing amounts of ethanol (up to 50%).

Yield: 2.62 gm (64% of theory),

M.P.: 101°–102° C.

EXAMPLE L 1-(7-Bromo-8-methoxy-1,3,4,5-tetrahydro-2H-3-benzazepin-2-on-3-yl)-3-chloro-propane (a) 8-Methoxy-1,3,4,5-tetrahydro-2H-3-benzazepin-2-one A solution of 56.8 gm (0.3 mol) of 8-methoxy-1,3-dihydro-2H-3-benzazepin-2-one (melting point: 190°–191° C.) dissolved in 600 ml of glacial acetic acid is hydrogenated for 12 hours in the presence of 5 gm of 10% palladium/charcoal at 80° C. under 5 bar. The catalyst is removed by suction filtration, and the acetic acid is distilled off in vacuo. The residue is mixed with water and then neutralized with potassium carbonate, and the precipitate obtained is subjected to suction filtration, washed with water, and dried.

Yield: 51.1 gm (89.1% of theory),

M P.: 160°–161° C. .

(b) 7-Bromo- and 9-bromo-8-methoxy-1,3,4,5-tetrahydro-2H-3-benzazepin-2-one

To 7.4 gm (0.04 mol) of 8-methoxy-1,3,4,5-tetrahydro-2H-3-benzazepin-2-one in 100 ml of 80% acetic acid, 6.4 gm=2.03 ml (0.04 mol) of bromine in 10 ml of glacial acetic acid are added dropwise at 3° to 5° C. with stirring. After 15 minutes the mixture is poured onto ice water and then neutralized with potassium carbonate, and the precipitate is subjected to suction filtration, washed with a small amount of water, and dried. The isomer mixture obtained is separated by chromatography over a column of silica gel (eluant: ethyl acetate).

Yield: 5.7 gm (52.8% of theory) of 9-bromo-isomer

IR-spectrum (methylene chloride): 3400 cm$^{-1}$ (NH), 1660 cm$^{-1}$ (C=O).

4.1 gm (39% of theory) of 7-bromo-isomer

IR-spectrum (calcium bromide): 3200 cm$^{-1}$ (NH), 1665 cm$^{-1}$ (C=O).

(c) 1-(7-Bromo-8-methoxy-1,3,4,5-tetrahydro-2H-3-benzazepin-2-on-3-yl)-3-chloro-propane An amount of 0.24 gm (5.5 mmol) of sodium hydride dispersion in oil (55%) is added to 1.35 gm (5 mmol) of 7-bromo-8-methoxy-1,3,4,5-tetrahydro-2H-3-benzazepin-2-one in 15 ml of dimethylsulfoxide, and the mixture is stirred for 30 minutes at ambient temperature and ten minutes at 35° to 40° C. The solution is added dropwise, with stirring, to 0.79 gm (5.5 mmol) of 1-bromo-3-chloropropane in 5 ml of dimethylsulfoxide with stirring. It is then stirred for two hours at ambient temperature, poured onto ice water, and extracted four times with methylene chloride. The methylene chloride extracts are washed several times with water, dried and concentrated in vacuo. The residue is purified over a silica gel column with ethyl acetate as eluant.

Yield: 210 mg (12% of theory),

M.P.: 119°–120° C.

EXAMPLE M 1-(7-Methoxy-1,3,4,5-tetrahydro-2H-3-benzazepin-2-on-3-yl)-3-chloro-propane (a) 7-Methoxy-1,3,4,5-tetrahydro-2H-3-benzazepin-2-one A quantity of 3.1 gm (0.0136 mol) of N-chloroacetyl-N-(2-(3-methoxy-phenyl)-ethyl)-amine is dissolved in 270 ml of ethanol and 1530 ml of water and illuminated for ten hours under a nitrogen atmosphere with a mercury high pressure lamp at 20° to 25° C. The solution is concentrated down to about 400 ml, mixed with sodium bicarbonate, and extracted several times with ethyl acetate. The extracts are dried over magnesium sulfate and concentrated by evaporation, and the residue is purified over a silica gel column with ethyl acetate as eluant.

Yield: 820 mg (31.5% of theory),

M.P.: 152°–154° C.

(b) 1-(7-Methoxy-1,3,4,5-tetrahydro-2H-3-benzazepin-2-on-3-yl)-3-chloro-propane

An amount of 1.15 gm (6 mmol) of 7-methoxy-1,3,4,5-tetrahydro-2H-3-benzazepin-2-one is dissolved in 30 ml of absolute tetramethylurea, mixed with 300 mg of 55% sodium hydride dispersion (in oil), and stirred for two hours at 20° to 25° C. under a nitrogen atmosphere. The reaction mixture obtained is added dropwise, with stirring, to 1.6 gm (7.8 mmol) of 1-chloro-3-iodopropane dissolved in 20 ml of tetramethylurea, at 15° to 20° C. under a nitrogen atmosphere, and the resulting mixture is stirred for three hours at ambient temperature. Then, about 300 ml of ethyl acetate are added, and the mixture is extracted six times with water. The organic solution is dried over magnesium sulfate and concentrated by evaporation, and the residue is purified over a silica gel column with methylene chloride and increasing quantities of ethanol (up to 2%).

Yield: 410 mg (25.5% of theory),
IR-spectrum (methylene chloride): 1650 cm$^{-1}$ (CO).

EXAMPLE N 1-(7-Nitro-8-methoxy-1,3,4,5-tetrahydro-2H-3-benzazepin-2-on-3-yl)-3-chloro-propane An amount of 28.5 gm (0.106 mol) of 1-(8-methoxy-1,3,4,5-tetrahydro-2H-3-benzazepin-2-on-3-yl)-3-chloro-propane is stirred in 350 ml of concentrated nitric acid for 30 minutes at 20° to 25° C. The solution is poured onto ice water, neutralized with potassium carbonate, and extracted twice with methylene chloride. The extract is dried over magnesium sulfate and concentrated by evaporation in vacuo, and the residue is purified over a silica gel column with ethyl acetate as eluant.

Yield: 11 gm (33.2% of theory),
M.P.: 127°–128° C.

EXAMPLE O

1-[2-(2-Amino-4,5-dimethoxy-phenyl)-ethylamino]-3-[N-methyl-N-(2-(indolyl-3)-ethyl)-amino]-propane (a)
2-[N-Methyl-N-(2-cyano-ethyl)-amino]-ethyl-indole-3

A quantity of 23.4 gm (0.135 mol) of 2-(N-methyl)-ethyl amino)indole-3 in 200 ml of absolute methanol and 8.9 ml (0.135 mol) of acrylonitrile is stirred at 50° C. for 40 minutes. After concentration in vacuo, the residue is purified over 800 gm of aluminium oxide (neutral; activity II-III) with methylene chloride and increasing amounts of ethanol (up to 3%) as eluant.

Yield: 20.8 gm (67.8% of theory),
IR-spectrum (methylene chloride): 2240 cm$^{-1}$ CN.

(b)
1-Amino-3-[N-methyl-N-(2-(indolyl)-3)-ethyl)-amino]-propane

Amounts of 7.6 gm (0.033 mol) of 2-[N-methyl-N-(2-cyanoethyl)-amino]-ethyl-indole-3 and 1.7 gm of Raney nickel in 70 ml of methanol saturated with ammonia are hydrogenated for two hours at 50° C. under 5 bar. After the catalyst has been filtered off and the residue has been concentrated by evaporation in vacuo, 7.7 gm of amine are obtained.

Yield: 7.7 gm (100% of theory).

(c)
1-[2-(4,5-Dimethoxy-2-nitro-phenyl)-1-oxoethyl-amino]-3-[N-methyl-N-(2-(indolyl-3)-ethyl-amino]-propane From a suspension of 7.2 gm (0.03 mol) of 4,5-dimethoxy-2-nitro-phenylacetic acid in 80 ml of absolute tetrahydrofuran, the imidazolide is prepared by the addition of 4.75 gm (0.03 mol) of N,N'-carbonyl-diimidazole. A solution of 8.2 gm (0.03 mol) of 1-amino-3-[N-methyl-N-(2-(indolyl-3)-ethyl)-amino]-propane in 60 ml of absolute tetrahydrofuran is added dropwise thereto, and after two hours' stirring at ambient temperature, the mixture is concentrated by evaporation, dissolved in methylene chloride, extracted with 2N sodium hydroxide solution, washed with water, dried over magnesium sulfate, again evaporated in vacuo, and purified over 800 gm of aluminium oxide (neutral; activity II-III) with methylene chloride and increasing amounts of ethanol (up to 4%).

Yield: 12.3 gm (90.9% of theory),
IR-spectrum (methylene chloride): 1670 cm$^{-1}$ CO.

(d)
1-[2-(2-Amino-4,5-dimethoxy-phenyl)-1-oxoethyl-amino]-3-[N-methyl-N-(2-(indolyl-3)-ethyl)-amino]-propane Fifteen grams (0.03 mol) of 1-[2-(4,5-dimethoxy-2-nitrophenyl)-1-oxoethyl-amino]-3-[N-methyl-N-(2-(indolyl-3)-ethylamino]-propane are dissolved in 160 ml of methanol, mixed with 0.8 gm of 10% palladium/charcoal, and hydrogenated for nine hours at ambient temperature under 5 bar. After the catalyst has been removed by suction filtration, the residue is concentrated by evaporation in vacuo and purified over 1200 gm of aluminium oxide (neutral; activity II-III) with methylene chloride and increasing amounts of ethanol (up to 12%).

Yield: 9.6 gm (75.6% of theory),
IR-spectrum (methylene chloride): 1655 cm$^{-1}$ CO.

(e)
1-[2-(2-Amino-4,5-dimethoxy-phenyl)-ethyl-amino]-3-[N-methyl-N-(2-(indolyl-3)-ethyl)-amino]-propane A solution of 4.3 ml (0.015 mol) of sodium bis-(2-methoxyethoxy)-dihydroaluminate (70% solution in toluene, about 3.5 molar) in 4 ml of absolute toluene is slowly added dropwise to a warm solution (at 60° C.) of 2.13 gm (0.005 mol) of 1-[2-2-amino-4,5-dimethoxyphenyl)-1-oxoethyl)-amino]-3-[N-methyl-N-(2-(indolyl-3)-ethyl)-amino]-propane in 35 ml of absolute dioxane under a nitrogen atmosphere, and then the mixture is refluxed for four hours. After decomposition with 1.8 ml of 10% ammonium chloride solution and 5 ml of 2 molar sodium hydroxide solution, the mixture is filtered, and the residue is concentrated by evaporation and purified over 120 gm of aluminium oxide (neutral; activity II-III) with methylene chloride and increasing amounts of ethanol (up to 3%) as eluant.

Yield: 2.05 gm (100% of theory).

EXAMPLE P 1-(1,3,4,5-Tetrahydro-2H-3-benzazepin-2,4-dion-3-yl)-3-chloropropane (a) 2-Amino-4-bromo-1H-3-benzazepine hydrobromide Prepared from 5.0 gm (0.032 mol) of o-phenylene diacetonitrile analogously to Example F(a).

Yield: 8.0 gm (78.6% of theory).

(b) 1,3,4,5-Tetrahydro-2H-3-benzazepin-2,4-dione

Prepared from 8.0 gm (0.025 mol) of 2-amino-4-bromo-1H-3-benzazepine hydrobromide analogously to Example F(b).

Yield: 3.7 gm (66.1% of theory),
M.P.: 189°–191° C.

(c) 1-(1,3,4,5-Tetrahydro-2H-3-benzazepin-2,4-dion-3-yl)-3-chloro-propane

A quantity of 3.5 gm (0.020 mol) of 1,3,4,5-tetrahydro-2H-3-benzazepin-2,4-dione is suspended in 30 ml of dimethylformamide and mixed with 2.5 gm of potassium tert.butoxide with stirring. After ten minutes, the solution obtained is added dropwise to 3.5 ml of 1-bromo-3-chloropropane in 20 ml of dimethylformamide while being cooled with ice. After one hour the mixture is poured onto ice water. A short time later the greasy precipitate crystallizes. The precipitate is subjected to suction filtration, dissolved in acetone, precipitated again with water, suction filtered, and dried.

Yield: 4.7 gm (90.4% of theory).

PREPARATION OF THE END PRODUCTS

EXAMPLE 1

1-(7,8-Dimethoxy-1,3,4,5-tetrahydro-2H-3-benzazepin-2-on-3-yl)-3-[N-methyl-N-(2-(indolyl-3)-ethyl)-amino]-propane A mixture of 2.98 gm (0.01 mol) of 1-(7,8-dimethoxy-1,3,4,5-tetrahydro-2H-3-benzazepin-2-on-3-yl)-3-chloro-propane, 1.39 ml (0.01 mol) of triethylamine, and 1.74 gm (0.01 mol) of 3-(N-methyl-2-amino-ethyl)-indole is stirred at 90° C. for four hours. The mixture is then dissolved in methylene chloride, extracted with 1% acetic acid, dried over magnesium sulfate, concentrated by rotation, and purified over a 150 gm silica gel column with methylene chloride and increasing amounts of ethanol (up to 10%).

Yield: 1.69 gm (38.8% of theory),
M.P.: 136°–140° C.

EXAMPLE 2

1-(7,8-Dimethoxy-1,3,4,5-tetrahydro-2H-3-benzazepin-1,2-dion-3-yl)-3-[N-methyl-N-(2-(indolyl)-3)-ethyl)-amino]-propane An amount of 0.41 gm (0.0036 mol) of selenium dioxide is added at 70° C. to a mixture of 17 ml of dioxane and 0.7 ml of water, stirred for 15 minutes and then mixed with 0.34 gm of kieselgur and 1.5 gm (0.034 mol) of 1-(7,8-dimethoxy-1,3,4,5-tetrahydro-2H-3-benzazepin-2-on-3-yl)-3-[N-methyl-N-(2-(indolyl-3)-ethyl)-amino]-propane. The mixture is refluxed for 46 hours, cooled, and filtered. The filtrate is concentrated by evaporation in vacuo, and the residue is purified over a silica gel column with methylene chloride with increasing amounts of ethanol (up to 20%) as eluant.

Yield: 0.15 gm (10% of theory),
M.P.: 55°–59° C.

EXAMPLE 3

1-(7,8-Dimethoxy-1,3,4,5-tetrahydro-2H-3-benzazepin-2-on-3-yl)-3-[N-methyl-N-(2-(5-methoxy-indolyl-3)-ethyl)-amino]-propane Prepared analogously to Example 1 by reaction of 1-(7,8-dimethoxy-1,3,4,5-tetrahydro-2H-3-benzazepin-2-on-3-yl)-3-chloropropane with 5-methoxy-3-(N-methyl-2-amino-ethyl)-indole.

Yield: 23.7% of theory,
M.P.: 55°–59° C.

EXAMPLE 4

1-(7,8-Dimethoxy-1,3,4,5-tetrahydro-2H-3-benzazepin-2-on-3-yl)-3-[N-(2-(indolyl-3)-ethyl)-amino]-propane A mixture of 0.6 gm (0.002 mol) of 1-(7,8-dimethoxy-1,3,4,5-tetrahydro-2H-3-benzazepin-2-on-3-yl)-3-chloro-propane and 3.2 gm (0.02 mol) of tryptamine is heated to 130° C. for one hour. After extraction with ethyl acetate/water, the organic phase is dried over magnesium sulfate, concentrated by evaporation in vacuo, and purified twice over 100 gm of aluminium oxide (neutral; activity II) with methylene chloride and increasing quantities of ethanol (up to 50%) as eluant.

Yield: 0.32 gm (38% of theory),
M.P.: 66°–67° C.

EXAMPLE 5

1-(7,8-Dimethoxy-1,3,4,5-tetrahydro-2H-3-benzazepin-2-thion-3-yl)-3-[N-methyl-N-(2-(indolyl-3)-ethyl)-amino]-propane Quantities of 2.18 gm (0.005 mol) of 1-(7,8-dimethoxy-1,3,4,-5-tetrahydro-2H-3-benzazepin-2-on-3-yl)-3-[N-methyl-N-(2-(indolyl-3)-ethyl)-amino]-propane and 1.5 gm (0.0037 mol) of 2,4-bis-(3-methoxyphenyl)-1,3-dithia-2,4-diphosphetan-2,4-disulfide are suspended in 10 ml of toluene and refluxed for three hours. The mixture is then concentrated by rotation and purified over 400 gm of aluminium oxide (neutral; activity II) with methylene chloride and with increasing amounts of ethanol (up to 5%).

Yield: 0.65 gm (28.8% of theory),
M.P.: 66°–71° C.

EXAMPLE 6

1-(1-Hydroxy-7,8-dimethoxy-1,3,4,5-tetrahydro-2H-3-benzazepin-2-on-3-yl)-3-[N-methyl-N-(2-(indolyl-3)-ethyl)-amino]-propane An amount of 0.15 gm (0.00033 mol) of 1-(7,8-dimethoxy-1,3,4,5-tetrahydro-2H-3-benzazepin-1,2-dion-3-yl)-3-[N-methyl-N-(2-(indolyl-3)-ethyl)-amino]-propane is dissolved in a mixture of methanol/water (95:5), mixed with 0.015 gm (0.0004 mol) of sodium borohydride, and stirred for 15 minutes at ambient temperature. The mixture is then acidified with 2N hydrochloric acid, made alkaline with methanolic ammonia, and filtered. The filtrate is concentrated by evaporation, taken up in methylene chloride, dried over magnesium sulfate, and concentrated again.

Yield: 9.11 gm (73.3% of theory),
Oil, Rf value: 0.24 (silica gel, methylene chloride+10% ethanol).

Calculated: C 69.16, H 7.37, N 9.31. Found: C 68.98, H 7.20, N 9.25.

EXAMPLE 7

1-(7,8-Dimethoxy-2,3,4,5-tetrahydro-1H-3-benzazepin-3-yl)-3-[N-methyl-N-(2-(indolyl-3)-ethyl)-amino]-propane A quantity of 2.18 gm (0.005 mol) of 1-(7,8-dimethoxy-1,3,4,-5-tetrahydro-2H-3-benzazepin-2-on-3-yl)-3-[N-methyl-N-(2-(indolyl-3)-ethyl)-amino]-propane is suspended in 30 ml of ether, and this suspension is added dropwise to a suspension of 0.75 gm (0.02 mol) of lithium aluminium hydride in 50 ml of ether. Then, the mixture is refluxed for eight hours, carefully combined with water and 15% sodium hydroxide solution, and subjected to suction filtration. The precipitate is washed with ethanol, dried, and purified over 300 gm of aluminium oxide (neutral; activity II) with methylene chloride.

Yield: 0.67 gm (31.9% of theory),

Oil, Rf value: 0.78 (aluminium oxide (neutral), methylene chloride+10% ethanol).

Calculated: C 74.07, H 8.37, N 9.97. Found: C 73.70, H 8.63, N 9.62.

EXAMPLE 8

1-(7,8-Dimethoxy-1,3,4,5-tetrahydro-2H-1,3-benzodiazepin-2-on-3-yl)-3-[N-methyl-N-(2-(indolyl-3)-ethyl)-amino]-propane Two grams (0.005 mol) of 1-[2-(2-amino-4,5-dimethoxy-phenyl)-ethyl-amino]-3-[N-methyl-N-(2-(indolyl-3)-ethyl)-amino]-propane and 1.0 gm (0.006 mol) of N,N'-carbonyldiimidazole are refluxed for 60 minutes in 40 ml of absolute ethyl acetate. After extraction with saturated potassium carbonate solution and water, the product which has been concentrated in vacuo is dissolved in methylene chloride and precipitated with petroleum ether.

Yield: 0.57 gm (26.1% of theory),

M.P.: 168°–169° C.

EXAMPLE 9

1-(7,8-Dimethoxy-1,3,4,5-tetrahydro-2H-3-benzazepin-2-on-3-yl)-3-[N-methyl-N-(2-(N-methyl-indolyl-3)-ethyl-amino]-propane Prepared analogously to Example 1 by reaction of 1-(7,8-dimethoxy-1,3,4,5-tetrahydro-2H-3-benzazepin-2-on-3-yl)-3-chloropropane with N-methyl-3-(N-methyl-2-amino-ethyl)-indole.

Yield: 18.0% of theory,

Oil, Rf value: 0.37 (silica gel, methylene chloride+10% ethanol).

Calculated: C 72.13, H 7.85, N 9.35. Found: C 71.92, H 7.80, N 9.22.

EXAMPLE 10

1-(7,8-Dimethoxy-1,3,4,5-tetrahydro-2H-3-benzazepin-2-on-3-yl)-3-[N-methyl-N-(2-(5-benzyloxy-indolyl-3)-ethyl)-amino]-propane Prepared analogously to Example 1 by reaction of 1-(7,8-dimethoxy-1,3,4,5-tetrahydro-2H-3-benzazepin-2-on-3-yl)-3-chloropropane with 5-benzyloxy-3-(N-methyl-2-amino-ethyl)-indole.

Yield: 10.4% of theory,

Oil, Rf value: 0.46 (aluminium oxide (neutral), methylene chloride+5% ethanol).

Calculated: C 73.17, H 7.26, N 7.76. Found: C 72.77, H 7.06, N 7.70.

EXAMPLE 11

1-(7,8-Dimethoxy-1,3,4,5-tetrahydro-2H-3-benzazepin-2-on-3-yl)-3-[N-methyl-N-(2-(5-hydroxy-indolyl-3)-ethyl)-amino]-propane Prepared analogously to Example 1 by reaction of 1-(7,8-dimethoxy-1,3,4,5-tetrahydro-2H-3-benzazepin-2-on-3-yl)-3-chloropropane with 5-hydroxy-3-(N-methyl-2-amino-ethyl)-indole.

Yield: 56.0% of theory,

M.P.: 68°–75° C.

EXAMPLE 12

1-(7,8-Dimethoxy-1,3,4,5-tetrahydro-2H-3-benzazepin-2-on-3-yl)-3-[N-methyl-N-(3-(indolyl-3)-propyl)-amino]-propane Prepared analogously to Example 1 by reaction of 1-(7,8-dimethoxy-1,3,4,5-tetrahydro-2H-3-benzazepin-2-on-3-yl)-3-chloropropane with 3-(N-methyl-3-amino-propyl)-indole.

Yield: 36.2% of theory,

M.P.: 49°–54° C.

EXAMPLE 13

1-(7,8-Dimethoxy-1,3,4,5-tetrahydro-2H-3-benzazepin-2-on-3-yl)-3-[N-methyl-N-(2-(5-bromo-indolyl-3)-ethyl)-amino]-propane Prepared analogously to Example 1 by reaction of 1-(7,8-dimethoxy-1,3,4,5-tetrahydro-2H-3-benzazepin-2-on-3-yl)-3-chloropropane with 5-bromo-3-(N-methyl-2-amino-ethyl)-indole.

Yield: 7.9% of theory,

M.P.: 74°–80° C.

EXAMPLE 14

1-(7,8-Dimethoxy-1,3,4,5-tetrahydro-2H-3-benzazepin-2-on-3-yl)-3-[N-methyl-N-(2-(7-methyl-indolyl-3)-ethyl)-amino]-propane Prepared analogously to Example 1 by reaction of 1-(7,8-dimethoxy-1,3,4,5-tetrahydro-2H-3-benzazepin-2-on-3-yl)-3-chloropropane with 7-methyl-3-(N-methyl-2-amino-ethyl)-indole.

Yield: 15.6% of theory,

M.P.: 62°–66° C.

EXAMPLE 15

1-(7,8-Dimethoxy-1,3-dihydro-2H-3-benzazepin-2-on-3-yl)-3-[N-methyl-N-(2-(indolyl-3)-ethyl)-amino]-propane Prepared analogously to Example 1 by reaction of 1-(7,8-dimethoxy-1,3-dihydro-2H-3-benzazepin-2-on-3-yl)-3-chloro-propane with 3-(N-methyl-2-amino-ethyl)-indole.

Yield: 17.7% of theory,

M.P.: 64°–70° C.

EXAMPLE 16

1-(1,3,4,5-Tetrahydro-2H-3-benzazepin-2,4-dion-3-yl)-3-[N-methyl-N-(2-(indolyl-3)-ethyl)-amino]-propane hydrochloride Prepared analogously to Example 1 by reaction of 1-(1,3,4,5-tetrahydro-2H-3-benzazepin-2,4-dion-3-yl)-3-chloro-propane with 3-(N-methyl-2-amino-ethyl)-indole and subsequent precipitation of the hydrochloride with ethereal hydrochloric acid.

Yield: 73.9% of theory,

M.P.: 91°–95° C.

EXAMPLE 17

1-(7,8-Dichloro-1,3,4,5-tetrahydro-2H-1,3-benzodiazepin-2-on-3-yl)-3-[N-methyl-N-(2-(N-methyl-5-benzyloxy-indolyl-3)-ethyl)-amino]-propane Prepared analogously to Example 8 by reaction of 1-[2-(2-amino-4,5-dichloro-phenyl)-ethyl-amino]-3-[N-methyl-N-(2-(N-methyl-5-benzyloxy-indolyl-3)-ethyl)-amino]-propane and N,N'-carbonyldiimidazole.

Yield: 37.4% of theory,

Oil, Rf value: 0.38 (aluminium oxide (neutral), methylene chloride+5% ethanol).

Calculated: C 65.84, H 6.06, N 9.91, Cl 12.54. Found: C 65.46, H 6.00, N 9.58, Cl 12.32.

The following compounds are obtained by use of procedures analogous to those of the above examples:

EXAMPLE 18

1-(7,8-Dimethoxy-2,3-dihydro-1H-3-benzazepin-3-yl)-3-[N-methyl-N-(2-(indolyl-3)-ethyl)-amino]-propane.

EXAMPLE 19

1-(7,8-Methylenedioxy-1,3,4,5-tetrahydro-2H-3-benzazepin-2-on-3-yl)-3-[N-methyl-N-(2-(indolyl-3)-ethyl)-amino]-propane.

EXAMPLE 20

1-(7,8-Dimethyl-1,3,4,5-tetrahydro-2H-3-benzazepin-2-on-3-yl)-3-[N-methyl-N-(2-(indolyl-3)-ethyl)-amino]-propane.

EXAMPLE 21

1-(7,8-Dichloro-1,3,4,5-tetrahydro-2H-3-benzazepin-2-on-3-yl)-3-[N-methyl-N-(2-(indolyl-3)-ethyl)-amino]-propane.

EXAMPLE 22

1-(7-Bromo-8-methoxy-1,3,4,5-tetrahydro-2H-3-benzazepin-on-2-on-3-yl)-3-[N-methyl-N-(2-(indolyl-3)-ethyl)-amino]-propane.

EXAMPLE 23

1-(7-Dimethylamino-8-methoxy-1,3,4,5-tetrahydro-2H-3-benzazepin-2-on-3-yl)-3-[N-methyl-N-(2-(indolyl-3)-ethyl)-amino]-propane.

EXAMPLE 24

1-(7-Methoxy-1,3,4,5-tetrahydro-2H-3-benzazepin-2-on-3-yl)-3-[N-methyl-N-(2-(indolyl-3)-ethyl)-amino-propane.

EXAMPLE 25

1-(7-Nitro-8-methoxy-1,3,4,5-tetrahydro-2H-3-benzazepin-2-on-3-yl)-3-[N-methyl-N-(2-(indolyl-3)-ethyl)-amino]-propane.

EXAMPLE 26

1-(1,3,4,5-Tetrahydro-2H-3-benzazepin-2-on-3-yl)-3-[N-methyl-N-(2-(indolyl-3)-ethyl)-amino]-propane.

The following examples illustrate a few pharmaceutical compositions comprising a compound of the present invention as an active ingredient and represent the best modes contemplated of using the invention. The compound 1-(7,8-dimethoxy-1,3,4,5-tetrahydro-2H-3-benzazepin-2-on-3-yl)-3-[N-methyl-N-(2-(indolyl-3)-ethyl)-amino]-propane has been used as the active substance. However, it should be understood that one or more other compounds of Formula I or the acid addition salts thereof can be used as active substance in place of said compound.

EXAMPLE 27

Tablets containing 10 mg of Active Substance

Each tablet has the following composition:

| Component | Amount (mg) |
| --- | --- |
| Active substance | 10.0 |
| Corn starch | 57.0 |
| Lactose | 48.0 |
| Polyvinyl pyrrolidone | 4.0 |
| Magnesium stearate | 1.0 |
| Total: | 120.0 |

Preparation:

The active substance, corn starch, lactose, and polyvinyl pyrrolidone are mixed together and moistened with water. The moist mixture is pressed through a screen with a 1.5 mm mesh and then dried at about 45° C. The dry granulate is passed through a screen with a mesh size of 1.0 mm and mixed with magnesium stearate. The finished mixture is compressed in a tablet press using punches 7 mm in diameter which are provided with a dividing slot, in order to form tablets.

Weight of tablet: 120 mg.

EXAMPLE 28

Coated Tablets containing 5 mg of Active Substance

Each tablet core has the following composition:

| Component | Amount (mg) |
| --- | --- |
| Active substance | 5.0 |
| Corn starch | 41.5 |
| Lactose | 30.0 |
| Polyvinyl pyrrolidone | 3.0 |
| Magnesium stearate | 0.5 |
| Total: | 80.0 |

Preparation:

The active substance, corn starch, lactose, and polyvinyl pyrrolidone are thoroughly mixed and moistened with water. The moist mass is pressed through a 1 mm screen and dried at about 45° C., and then the granulate is passed through a screen again. After the magnesium stearate has been added, convex tablet cores with a diameter of 6 mm are pressed out in a tablet-making machine. The tablet cores thus produced are covered in known manner with a coating consisting essentially of sugar and talc. The finished coated tablets are polished with wax.

Weight of tablet: 130 mg.

EXAMPLE 29

Ampules containing 2.5 mg/ml of Active Substance

Each ampule contains the following:

| Component |  | Amount |
| --- | --- | --- |
| Active substance |  | 5.0 mg |
| Sorbitol |  | 50.0 mg |
| Distilled water | q.s. ad | 2.0 ml |

Preparation:

The active substance is dissolved in water for injection in a suitable vessel, and the solution is made isotonic with sorbitol.

After filtering through a membrane filter, the solution is decanted into cleaned, sterilized ampules under a current of nitrogen and heated in an autoclave for 20 minutes in a current of water vapor.

EXAMPLE 30

Suppositories containing 15 mg of Active Substance

Each suppository has the following composition:

| Component | Amount (mg) |
|---|---|
| Active substance | 15.0 |
| Suppository mass (e.g., WITEPSOL ® H19 or W45, available from Chemische Werke Witten GmbH) | 1685.0 |
| Total: | 1700.0 |

Preparation:

The suppository mass is melted, and after the molten mass has been cooled to 38° C., ground active substance is homogeneously dispersed therein. The molten mass is then cooled to 35° C. and poured into slightly chilled suppository molds.

Weight of one suppository: 1.7 gm.

EXAMPLE 31

Drops containing 2 mg/ml of Active Substance

One hundred milliliters of drop solution has the following composition:

| Component | Amount |
|---|---|
| Active substance | 0.20 gm |
| Hydroxyethyl cellulose | 0.15 gm |
| Tartaric acid | 0.10 gm |
| Sorbitol solution containing 70% dry matter | 30.0 gm |
| Glycerol | 10.0 gm |
| Benzoic acid | 0.15 gm |
| Distilled water | q.s. ad 100.0 ml |

Preparation:

The distilled water is heated to 70° C. Hydroxyethyl cellulose, benzoic acid, and tartaric aicd are dissolved therein with stirring. The mixture is cooled to ambient temperature, and the glycerol and sorbitol solution are added with stirring. The active ingredient is added at ambient temperature and stirred until completely dissolved. The solution is then evacuated in order to eliminate air from the liquid, with stirring.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

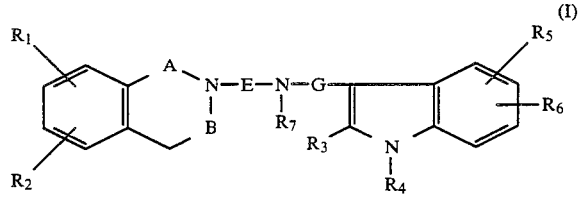

(I)

wherein

A represents a $-CH_2-CH_2-$, $-CH=CH-$, $-NH-CO-$, or $-CH_2-CO-$ group and B represents a methylene, carbonyl, or thiocarbonyl group or A represents a $-CO-CO-$ or

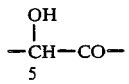

group and B represents a methylene group,

E represents a linear alkylene group having from 2 to 4 carbon atoms, optionally substituted by an alkyl group having from 1 to 3 carbon atoms, or a 2-hydroxy-n-propylene, 2-hydroxy-n-butylene, or 3-hydroxy-n-butylene group, G represents a linear alkylene group having from 1 to 5 carbon atoms, optionally substituted by an alkyl group having from 1 to 3 carbon atoms, $R_1$ represents a hydrogen, chlorine, or bromine atom or a trifluoromethyl, nitro, amino, alkylamino, dialkylamino, alkyl, hydroxyl, alkoxy, or phenylalkoxy group, where each alkyl moiety may have from 1 to 3 carbon atoms, $R_2$ represents a hydrogen, chlorine, or bromine atom or a hydroxyl, alkoxy, phenylalkoxy or alkyl group, where each alkyl moiety may have from 1 to 3 carbon atoms, or $R_1$ and $R_2$ together represent an alkylenedioxy group having 1 or 2 carbon atoms, $R_3$ represents a hydrogen, chlorine, or bromine atom or an alkyl group having from 1 to 4 carbon atoms, $R_4$ represents a hydrogen atom or an alkyl or phenylalkyl group, where each alkyl moiety may have from 1 to 3 carbon atoms, $R_5$ represents a hydrogen, fluorine, chlorine, or bromine atom or an alkyl, hydroxyl, alkoxy, or phenylalkoxy group, where each alkyl moiety may have from 1 to 3 carbon atoms, $R_6$ represents a hydrogen atom or an alkoxy group having from 1 to 3 carbon atoms, and $R_7$ represents a hydrogen atom, an alkenyl group having from 3 to 5 carbon atoms, or an alkyl or phenylalkyl group, where each alkyl moiety may have from 1 to 3 carbon atoms, or an acid addition salt thereof.

2. A compound of claim 1 of the formula

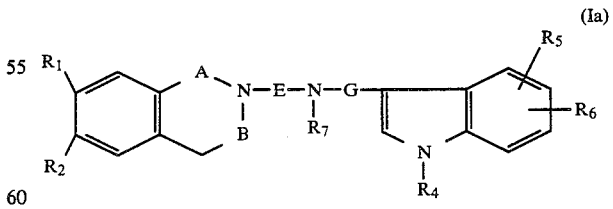

(Ia)

wherein

A and B are defined as in claim 1,

E represents an n-propylene group,

G represents an ethylene or n-propylene group, $R_1$ represents a chlorine or bromine atom or a methyl, methoxy, nitro, amino, methylamino, or dimethylamino group, $R_2$ represents a hydrogen, chlorine, or bromine atom or a methoxy group, or $R_1$ and $R_2$ together represent a methylenedioxy group, $R_4$ represents a hydrogen atom or a methyl group, $R_5$ represents a hydrogen, fluorine, chlorine, or bromine atom or a methyl, hydroxyl, methoxy, or benzyloxy group, $R_6$ represents a hydrogen atom or a methoxy group, and $R_7$ represents a hydrogen atom or a methyl group, or an acid addition salt thereof.

3. A compound of claim 2, wherein

A represents a —CH$_2$CH$_2$— or —CH═CH— group and B represents a carbonyl group or A represents a —COCO— or —NH—CO— group and B represents a methylene group, E represents an n-propylene group, G represents an ethylene group, $R_1$ and $R_2$ each represent a methoxy group, $R_4$, $R_5$, and $R_6$ each represent a hydrogen atom, and $R_7$ represents a methyl group, or an acid addition salt thereof.

4. 1-(7,8-Dimethoxy-1,3,4,5,tetrahydro-2H-3-benzazepin-2-on-3-yl)-3-[N-methyl-N-(2-(indolyl-3)-ethyl-amino]-propane or an acid addition salt thereof.

5. 1-(7,8-Dimethoxy-1,3,4,5-tetrahydro-2H-3-benzazepin-1,2-dion-3-yl)-3-[N-methyl-N-(2-(indolyl-3)-ethyl)-amino]-propane or an acid addition salt thereof.

6. A compound of claim 1 which is a pharmacologically acceptable acid addition salt with an inorganic or organic acid.

7. A pharmaceutical composition comprising as active ingredient an effective amount of at least one compound of claim 1 and pharmacologically acceptable carrier and/or diluent.

8. A process for treating sinus tachycardia or ischaemic heart disease in a host which comprises administering to a host in need of such treatment an effective amount of at least one compound of claim 1.

* * * * *